US00PP11103P

United States Patent [19]

Carruth

[11] Patent Number: Plant 11,103

[45] Date of Patent: Oct. 19, 1999

[54] FLORIBUNDA ROSE PLANT NAMED 'WEKCRYREG'

[75] Inventor: Thomas F. Carruth, Altadena, Calif.

[73] Assignee: Weeks Wholesale Rose Grower, Inc., Upland, Calif.

[21] Appl. No.: 09/049,467

[22] Filed: Mar. 27, 1998

[51] Int. Cl.[6] ..... A01H 5/00

[52] U.S. Cl. ..... Plt./141

[58] Field of Search ..... Plt./141, 144, 148

*Primary Examiner*—Howard J. Locker

*Attorney, Agent, or Firm*—Christie, Parker & Hale, LLP

[57] ABSTRACT

A new variety of hybrid floribunda rose suitable for garden decoration, having flowers of ivory coloration with pink centers.

1 Drawing Sheet

BACKGROUND OF THE INVENTION

This invention relates to a new and distinct variety of Floribunda rose. The varietal denomination of the new variety is 'Wekcryreg'. It has as its seed parent the variety known as 'Arobipy' (U.S. Plant Pat. No. 6,714) and as its pollen parent the variety known as 'Macyoumis'.

SUMMARY OF THE INVENTION

Among the features which distinguish the new variety from other presently available and known commercial rose cultivars are the following combination of characteristics: its lighter colored zone on the peduncle just below the hypanthium, its deeply colored innermost petals and petaloids, its greenish coloration in the outer petals that increases as the petals age, its bright red styles and its extremely prickly leaf rachis. The plant is a bushy upright growing plant, suitable for outdoor garden decoration.

Asexual reproduction of the new variety by budding as performed in Kern County and Upland, Calif., shows that the foregoing and other distinguishing characteristics come true to form and are established and transmitted through succeeding propagations. 'Wekcryreg' may be asexually propagated by cuttings, budding or grafting.

COMPARISON WITH PARENTS

The new rose may be distinguished from its seed parent, 'Arobipy' by the following combination of characteristics: whereas 'Wekcryreg' bears medium sized flowers of a white coloration with a few dark pink inner petals, 'Arobipy' bears significantly larger flowers of a pure white coloration. The mature growth habit of the seed parent is a tall upright bush, whereas the mature growth habit of the new variety is significantly shorter and may result in a more rounded bush.

The new variety may be distinguished from its pollen parent, 'Macyoumis' by the following combination of characteristics: whereas 'Wekcryreg' bears white flowers with a few dark pink inner petals, 'Macyoumis' bears flowers of a uniform pink coloration with a white reverse. The pollen parent bears flowers with about 25 petals, whereas the new variety bears flowers of significantly more double petalage (about 34 to 42). The mature growth habit of 'Macyoumis' is a very compact short bush, whereas the mature growth habit of 'Wekcryland' is signficantly larger in height and diameter.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout this specification, color values are based upon the Colour Chart of The Royal Horticultural Society of London, England, except where common terms of color definition are employed.

DESCRIPTION OF THE NEW VARIETY

The following description is of rose plants of the new cultivar grown outdoors in Upland, Calif. in the month of October. Phenotypic expression may vary with environmental, cultural and climatic conditions, as well as differences in conditions of light and soil.

FLOWER

The new variety sometimes bears its flowers singly, usually in clusters of three to four or more per stem. Flowers are borne in irregular flat to somewhat rounded clusters on normal medium length stems (about 32 to about 46 cms.). Outdoors, the plant blooms very abundantly and nearly continuously during the growing season. The flowers have a slight tea to apple-like fragrance.

BUD

The peduncle is about 3.5 to about 5 cms. in length, of slender to average caliper, and usually stiff. It is moderately smooth, with very few stipitate glands and numerous fine hairs. Peduncle color is between 144A and 146A at the base, often lightening to between 145A and 151C just below the hypanthium. Hypanthium color is between 144A and 146A.

Before the calyx breaks, the bud is about 1.2 to about 1.5 cm. in diameter at the widest point, about 1.8 to about 2.2 cms. in length, and very pointed to ovoid in shape. The surface of the bud bears few stipitate glands and numerous fine hairs, usually with slender serrate to irregularly cut foliaceous parts extending beyond the tip of the bud equal to ¾ or more of its length. Bud color is between 144A and 146B.

The inner surface of the sepals is covered with fine wooly tomentum; sepal margins are lined with many stipitate glands and some slender foliaceous parts.

As the petals open (after the calyx breaks), the bud is about 1.4 to about 1.8 cms. in diameter at the widest point, about 2.2 to about 2.6 cms. in length, and very pointed to ovoid in form. The color of the under surfaces of the newly opened petals is between 155D and 157D sometimes finely edged with between 55B and 63C. The color of the upper surfaces of the newly opened petals is between 155D and 56C sometimes with finely edged with between 55B and 63C. At the point where the petal attaches, there is a moderately small zone of near 145B.

BLOOM

When fully open, the bloom ranges from about 7 to about 8.5 cms. in diameter. Petalage is fully double with about 34 to 42 petals and about 3 to 7 petaloids arranged irregularly. When partially open, the bloom form is moderately high centered to somewhat cupped. The petals are somewhat loosely spiraled with petal edges moderately reflexed outward. When fully open, the bloom form is more cupped to full. The petals are more loosely cupped to undulated with petal edges rolled to very reflexed outward.

PETALS

The substance of the petals is moderately heavy and moderately thick, with upper surfaces slightly satiny and under surfaces slightly shiny. The outer petals are nearly round to broadly obovate in shape with apices very rounded to sometimes slightly mucronate. The inner petals are more obovate in shape with apices very rounded to sometimes slightly mucronate.

NEWLY OPENED FLOWER

The under surface of the outer petals is between 155A and 155D. The upper surface of the outer petals is between 155A and 155D sometimes very lightly suffused and very finely edged with between 56D and 62D. At the point where the petal attaches, there is a moderately small zone of between 150D and 145D.

The under surface of the intermediate petals is between 155A and 155D. The upper surface of the intermediate petals is between 155A and 155D sometimes lightly suffused between 56D and 62D and sometimes irregularly marked with as dark as between 55C and 62C. At the point where the petal attaches, there is a moderately small zone of between 150D and 145D.

The under surface of the inner petals is between 155A and 155D. The upper surface of the inner petals is between 155A and 155D often moderately suffused with between 55D and 62C and often irregularly marked with as dark as between 55A and 63B. At the point where the petal attaches, there is a moderately small zone of between 150D and 145D.

The under surface of the innermost petals and petaloids, is between 155A and 155D. The upper surface of the innermost petals and petaloids is between 155A and 155D usually deeply suffused with between 55C and 62B and usually irregularly marked with as dark as between 55A and 63B. At the point where the petaloid attaches, there is a moderately small zone of between 150D and 145D.

The general tonality of the newly opened flower is between 155A and 155D on the outer and intermediate petals suffusing to between 55D and 62C on the inner petals and usually irregularly marked with as deep as between 55A and 63B on the innermost petals and petaloids.

THREE DAY OLD FLOWER

The under and upper surface of the outer petals is between 155A and 157D. At the point where the petal attaches, there is no zone of different coloration. The under surface of the intermediate petals is between 155A and 155D. The upper surface of the intermediate petals is between 155A and 155D sometimes lightly suffused with between 56D and 62D and sometimes irregularly marked with as dark as between 55C and 62C. At the point where the petal attaches, there is no zone of different coloration.

The under surface of the inner petals is between 155A and 155D. The upper surface of the inner petals is between 155A and 155D often moderately suffused with between 56A and 62 C and often irregularly marked with as dark as between 55B and 63B. At the point where the petal attaches, there is no zone of different coloration.

The under surface of the innermost petals and petaloids is between 155A and 155D. The upper surface of the innermost petals and petaloids is between 155A and 155D usually deeply suffused with between 55C and 62B and usually irregularly marked with as dark as between 55B and 63C. At the point where the petal attaches, there is no zone of different coloration.

The general tonality of the newly opened flower is between 155A and 157D on the outer petals, between 155A and 155D on the intermediate petals suffusing to between 56A and 62C on the inner petals and usually irregularly marked with as deep as between 55B and 63C on the innermost petals and petaloids.

On the spent bloom, the petals usually persist. The white portion of the outer and intermediate petals picks up more green tones to as dark as between 157C and 157D before dropping away.

In October in Upland, Calif., blooms on the bush growing outdoors generally last about five or more days. Cut roses from plants grown outdoors and kept at normal indoor living temperatures generally last about five or more days.

MALE REPRODUCTIVE ORGANS

Stamens are average to many in number (approximately 120) and are arranged regularly about the pistil; a few are mixed with petaloids. The filaments are of irregular lengths, most with anthers. Filaments are near 1C. The anthers are medium in size for the class and all open approximately at the same time. Anther color is near 16B when immature and near 166B at maturity. Pollen is moderately abundant and near 12D in color.

FEMALE REPRODUCTIVE ORGANS

Pistils vary in number (approximately 70). The styles are moderately even, short to average in length, somewhat thin to average in caliper, and loosely bunched. Stigma color is between 160C and 6D. Style color is between 42A and 34A. Ovaries are usually all enclosed in the calyx.

Hips have not been observed on this variet when grown in Upland, Calif.

FOLIAGE

The compound leaves are usually comprised of three to five and sometimes seven leaflets and are borne abundantly. The leaves are about 7 to about 12 cms. in length and about 6 to about 8 cms. in width at the widest point, moderately heavy in texture, and semi-glossy to somewhat rugose in finish. The leaflets are about 3.3 to about 5.2 cms. in length and about 1.7 to about 3.8 cms. in width at the widest point, broadly oval in shape with acute to somewhat acuminate apices and acute bases. Their margins are sometimes simply to often doubly serrate.

The upper surface of the mature leaf is between 147A and 139A. The under surface of the mature leaf is between 147B and 138A. The upper surface of the young leaf is between 144A and 146B, sometimes suffused with between 183A and 187B. The under surface of the young leaf is between 144B and 146C, sometimes heavily suffused with between 183A and 187B.

The rachis is moderately heavy in caliper and somewhat rough. The upper side is moderately grooved with many stipitate glands on the edges of the grooves. The under side of the rachis iis very rough with a few stipitate glands and many irregularly sized small pickles distributed along the full length. Prickle shape and coloration is similar to the prickles on the new growth. Rachis color is between 144A and 146B. The edges of the grooves are sometimes suffused with between 183A and 187B.

The stipules are about 1.7 to about 2.3 cms. in length, of medium width and with medium length straight point that usually turn out at an angle of more than 45 degrees.

The plant displays an above average degree of resistance to powdery mildew and rust as compared to other commercial varieties grown under comparable conditions in Upland, Calif.

GROWTH

The plant has a bushy upright medium height growth habit (about 100 to about 150 cms. in height and about 80 to about 120 cms. spread at the widest point), with very full branching. It displays very vigorous growth and the canes are of medium to heavy caliper for the class.

The color of the major stems is between 146C and 152A. They bear several large prickles which are about 0.7 to about 1.3 cms. in length. The large prickles are almost straight angled very slightly downward with a somewhat long narrow oval shaped base; prickle color is between 164B and 165C. The major stem bears few small prickles of similar shape and coloration.

The color of the branches is between 146A and 137C. They bear many large prickles which are of similar size and shape to the large prickles on the major stems; prickle color is between 160B and 162C, sometimes lightly suffused with near 174A. The branches bear few many small prickles of similar shape and coloration.

The color of the new shoots is between 144A and 146B, sometimes suffused with between 183A and 187B. They bear many large prickles which are of similar size and shape to the large prickles on the major stems; prickle color is between 160B and 162C. The shoots bear many small prickles of similar shape and coloration.

I claim:

1. A new and distinct variety *Floribunda rose* plant substantially as described and illustrated herein.

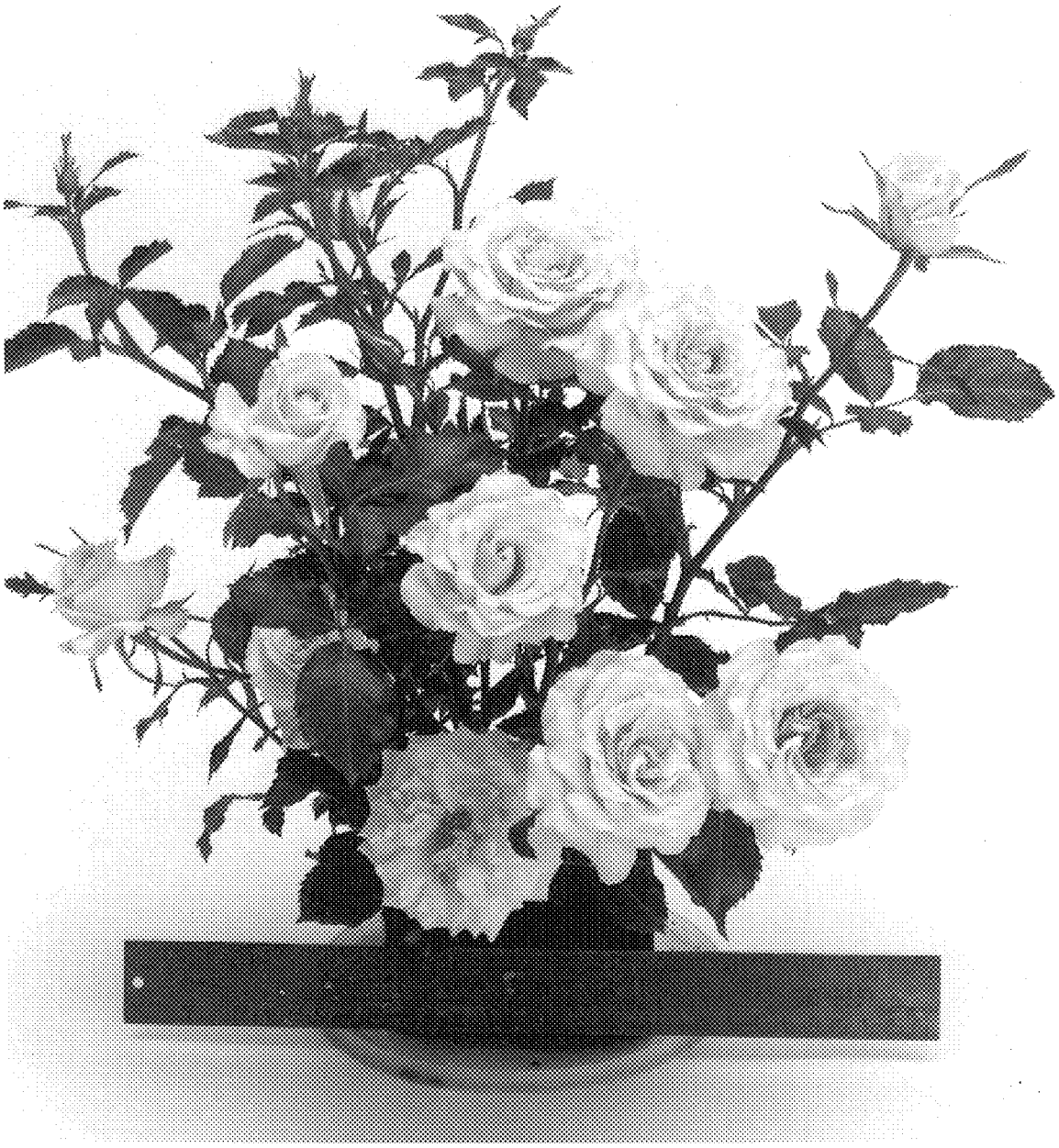

* * * * *